United States Patent [19]

Wardle

[11] Patent Number: 4,748,969
[45] Date of Patent: Jun. 7, 1988

[54] MULTI-LUMEN CORE DEFLECTING ENDOSCOPE

[75] Inventor: John L. Wardle, Shelton, Conn.

[73] Assignee: Circon Corporation, Santa Barbara, Calif.

[21] Appl. No.: 47,687

[22] Filed: May 7, 1987

[51] Int. Cl.⁴ .............................................. A61B 1/00
[52] U.S. Cl. ........................................ 128/4; 138/120
[58] Field of Search ...................... 128/3, 4, 5, 6, 7; 350/96.26; 138/120

[56] References Cited

U.S. PATENT DOCUMENTS

| | | | |
|---|---|---|---|
| 1,958,656 | 5/1934 | Buerger | 128/7 |
| 2,120,996 | 6/1938 | Wappler | 128/7 |
| 3,368,552 | 2/1968 | Bottcher | 128/4 |
| 3,610,231 | 10/1971 | Takahashi et al. | 128/6 |
| 3,792,701 | 2/1974 | Kloz et al. | 128/7 |
| 3,918,438 | 11/1975 | Hayamizu et al. | 128/4 |
| 4,530,568 | 7/1985 | Haduch et al. | 128/6 X |

Primary Examiner—William H. Grieb
Attorney, Agent, or Firm—Perman & Green

[57] ABSTRACT

An endoscope having a control head, an objective head and a flexible shaft therebetween. The shaft has a flexible core with a conduit means therewith. A deflection means is provided with the shaft having a tension member and a distal end compression member for controllably returning the distal end to an undeflected position.

20 Claims, 4 Drawing Sheets

MULTI-LUMEN CORE DEFLECTING ENDOSCOPE

BACKGROUND OF THE INVENTION

1. Field of the Invention

This invention relates to flexible inspection instruments for use in both industrial and medical applications and, more particularly, to an elongated, flexible, fiberscopic inspection device having a substantially flexible shaft and a deflection means therewith.

2. Prior Art

Elongated tubular inspection devices, particularly such devices incorporating flexible fiber-optics, are often used to inspect sites which would not normally be visible to the human eye. One application of such tubular inspection devices is in the practice of medicine. For instance, a common form of such device, known as a flexible ureteropyeloscope, is used for the inspection of the human ureter and entire kidney area while a similarly structured device, known as a colonscope, is used for the inspection of the colon.

The ureteropyeloscope is conventionally used for a variety of functions such as observation of areas and presenting a working tool at the area for such things as removing ureteral or kidney stones, dislodgement or electro-hydraulic destruction of ureteral stones, taking biopsies, irradiating tumors with laser fibers, etc. The ureteropyeloscope examination can involve the physician's placing the instrument in the body through the urethra, then into the bladder, then through one of the ureteral tubes and then, if necessary, into the kidney itself. This can usually be a time consuming and potentially tortuous path through several organs of the body.

The inspection instrument generally has a control head forming a proximal end and a flexible tubular shaft, the end of which forming a distal end. The physician observes target areas through an eyepiece in the control head. Generally, the ureteropyeloscope is provided with a bundle or bundles of optical fibers which bring light to its objective end, the end which is placed adjacent the area to be examined, and a bundle or bundles of light transmitting fibers through which an image of the examined area is transmitted back to the eyepiece. The ureteropyeloscope can generally further incorporate a channel which provides a conduit for providing washing fluid to the site under examination as well as for the introduction of accessory devices to the site such as a biopsy forceps.

The flexible tubular shaft extending between the proximal end and the distal end of the flexible instrument generally has a variety of components passing therethrough. The shaft may have such components as a fiber bundle, a working channel and distal end control wires. The tubular shafts can also have a variety of cross sectional shapes as is seen from U.S. Pat. Nos. 1,958,656; 2,120,996; 3,368,552; 3,792,701 and 3,918,438.

The control head of a flexible ureteropyeloscope is generally capable of serving many purposes including housing the optical eyepiece assembly, providing an entry for a light carrier from a light source, housing a deflection control system for moving and controlling the distal end and providing an entry for tools and fluids to enter into the control head and be transported to the objective end by means of the working channel. One such control head is described in co-pending U.S. patent application Ser. No. 017,813 filed Feb. 24, 1987 entitled "Improved Instrument Control Head" by the same inventor as the present application, which is incorporated by reference in its entirety herein.

One type of deflectable flexible inspection instrument is described in U.S. Pat. No. 4,530,568 by Haduch et al. entitled "Flexible Optical Inspection System" assigned to the same assignee as herein. In the instrument in that patent, ribs or vertebrae 54 and 55 are used to impart limited flexibility and sufficient rigidity to the instrument to provide a structure which is deflectable. However, instruments which require ribs for structural integrity have a practical limit on the smallness of their cross-sectional area. In addition, deflectable instruments which use a rib-like frame in their shafts also require protective sheaths around their fiber-optic bundles and control cables which further increases the cross-sectional size of their shafts.

A consideration arises in using presently available inspection instruments in that the cross-section size of the shafts are often too large in which to properly enter or pass through certain cavities or channels to reach a target area.

A further consideration arises in using presently available devices in that it often takes a relatively long period of time to reach a target area because of the relatively large cross-sectional size of the shaft in relation to the channels in which the shaft must pass through.

A further consideration arises in using presently available medical devices in that balloon dilation of channels must be used to expand certain channels such that a relatively large cross-sectional shaft can pass therethrough.

A further consideration arises in using presently available medical devices in that a patient's discomfort and risk of complications may be unreasonably high due to balloon dilation of channels such that the channel can pass a relatively large cross-sectional size shaft.

A further consideration arises in using presently available devices in that reasonably sized shafts generally do not possess a distal end deflection means in order to negotiate through tortuous paths and access various target areas.

A further consideration arises in using presently available devices having relatively small cross-sectional shafts in that little or no torque stability is generally provided to allow twisting of the instruments while maintaining registry between the proximal end and the distal end.

A further consideration arises in using presently available devices having relatively small cross-sectional shafts in that no compact distal end deflection means is provided.

SUMMARY OF THE INVENTION

The foregoing problems are overcome and other advantages are provided by an instrument of a generally tubular shape for accessing a target area. The instrument may have a shaft with a substantially flexible core and a deflection means disposed within the core for controllably deflecting the distal end of the instrument.

In accordance with one embodiment of the invention, the tubular flexible instrument comprises a control head forming a proximal end, an objective head forming a distal end and a tubular flexible shaft therebetween. The flexible shaft comprises a structural core of a flexible material having a first longitudinal axis and a conduit means therewith. A deflection means is disposed with the core means and is offset from the first longitudinal axis proximate to the distal end of the instrument and is connected to a control means proximate the control head.

In a preferred embodiment, the deflection means comprises a tension cable coaxially mounted with a distal spring deflection recovery member whereby upon increased tension in the tension member, the flexible shaft can deflect by compressing the spring member and allowing the flexible core to bend or undergo an unequal cross-sectional deformation. The shaft further comprises a distal deflection recovery means to assist in automatically returning the shaft to an undeflected position upon inactivation of the control means.

Alternatively or additionally, a proximal second spring means can be provided for reducing the tension in the tension means upon inactivation of the control means and thereby acting as a deflection recovery.

A shaft torque stabilizer means may also be provided, such as a wire braid sheath with an outer protective covering. The sheath can be selectively connected to the core means to allow for proper deflection agility in the shaft. In yet a further embodiment, the deflection means can comprise a compressingly stable connection member which is connected to the distal end of the instrument and is offset from the first longitudinal axis proximate the distal end. The distal end can be deflected by applying a compressive force to the connection member thereby applying an offset force to the distal end to deform the core and deflect the shaft.

BRIEF DESCRIPTION OF THE DRAWINGS

The foregoing aspects and other features of the invention are explained in the following description, taken in connection with the accompanying drawings where.

DETAILED DESCRIPTION OF THE INVENTION

Figure 1:
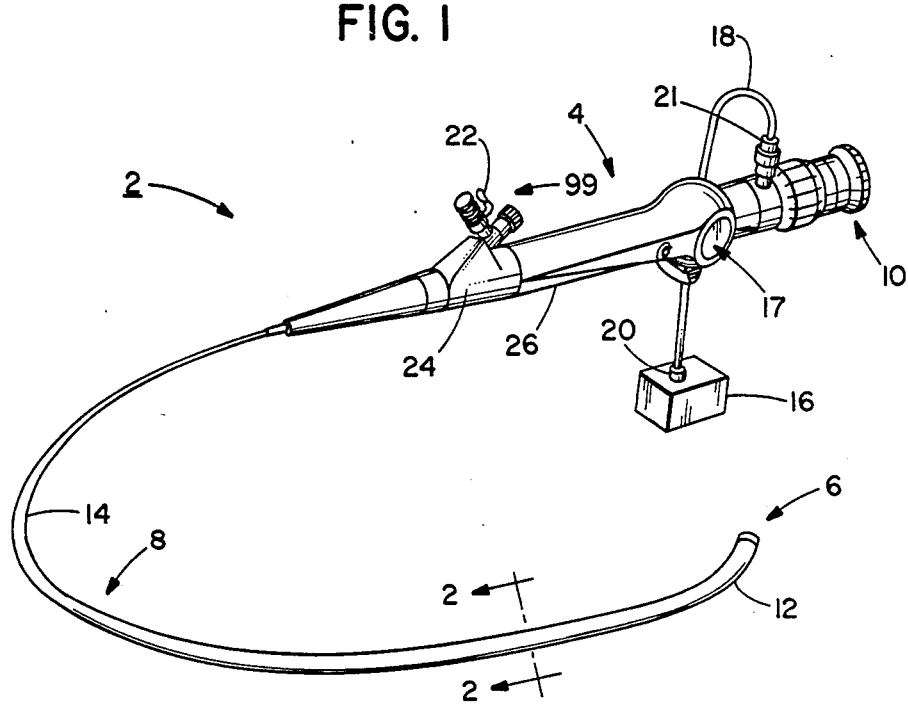
FIG. 1 is a perspective view of a flexible inspection instrument incorporating features of the present invention.

Referring to FIG. 1, there is shown one embodiment of a flexible inspection instrument 2, incorporating features of the invention. The inspection instrument 2, in this embodiment, is a flexible ureteropyeloscope which is generally for internal examinations and operations on the human body and more particularly for use in the ureter and kidney area of the body. The ureteropyeloscope 2 has a proximal control head 4 having a housing 26, a distal objective head 6 and a tubular flexible shaft 8 interconnecting the control head 4 to the objective head 6.

The tubular flexible shaft 8 is generally capable of conveying the objective head 6 to the site to be examined and is also capable of defining a tubular passage 32 (see FIG. 2) for elongate components extending through the shaft from the entry port 99 control head 4 to the objective head 6. The tubular flexible shaft 8 includes a relatively short distal deflector section 12 connected to the objective head 6 and an extended proximal flexible section 14 between the distal deflector section 12 and the control head 4. As will be described below the distal deflector section 12 is adjustable in a controlled manner from the control head 4 via a deflection control 17 for mainpulating the objective head 6 over the entire site, such as a body cavity, being examined and to this end has a high degree of flexibility. The flexible shaft section 14, however, can be less flexible, being required to flex only sufficiently to follow the contours of the canal or tract leading to the target area.

Figure 2:
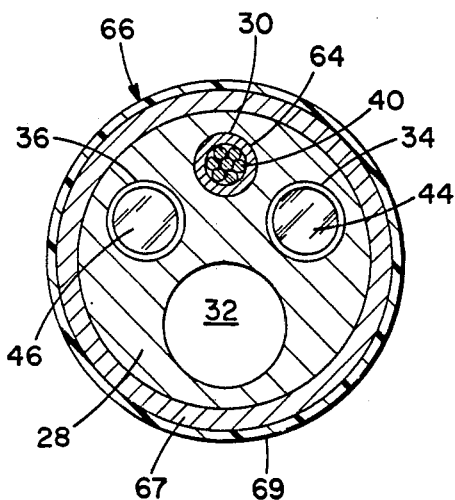
FIG. 2 is a cross-sectional view of the shaft in FIG. 1 taken along line 2—2.

For inspecting the site to be examined, in this embodiment, the ureteropyeloscope has an optical system including an external light carrier or bundle of light transmitting fibers 18 for carrying light from a lamp box or light source 16 for illuminating the inspection site. Light carrier 18 is conected to the lamp box 16 by lamp box connector 20. In the embodiment shown, the carrier 18 has a control head connector 21 which connects to a rotatable combination light post/vent valve assembly 22 on the control head 4. A first light carrier 44 (see FIG. 2) is located in the instrument 2 and receives light from the external light carrier 18 at the light post/vent valve assembly 22. The first internal light carrier 44 travels through the control head 4 and through the flexible shaft 8 (as shown in FIG. 2) to the objective head 6. The carrier 44 then provides light to the inspection site. A light image received from the illuminated site is conveyed back to an eyepiece assembly 10 by a second internal light carrier 46 (see FIG. 2) and suitable optical system (not shown). Using the eyepiece assembly 10 the physician or clinician can view the operative field and follow the movement of the distal end of the flexible shaft relative to the operative field. The accessory passage or working channel 32 extends from the control head 4 through the flexible shaft 8 to terminate in an open end in the objective head 6 and is accessible through an entry port 99 mounted on an rotatable entry block 24 of the control head 4.

Referring now also to FIG. 2, a cross-sectional view of the shaft 8 of the instrument in FIG. 1 is shown. In the embodiment shown, the shaft 8 has a single structural core 28 made of a flexible material also known as a multi-lumen core. In a preferred embodiment, the core 28 is made of an extruded polymer material such as polyurethane; however, any suitable type of flexible and resilient material can be used. The core 28 generally extends between the control head 4 and the objective head 6. Although flexible and resilient, the core 28 has a longitudinal axis with sufficient rigidity to establish a flexible structural frame for the shaft 8.

Located within the core 28, in the embodiment shown, are four conduits or passageways; a deflection conduit 30, a working conduit 32, and two fiber-optic conduits 34 and 36, which travel through the core 28 from a first end 37 (see FIG. 3) of the core 28 adjacent the control head 4 to a second end 38 (see FIG. 3) of the core 28 adjacent the objective head 6. The conduits 30, 32, 34, 36 are substantially continuous between the two ends 37 and 38 of the core 28; however, their paths may be either straight, curved or even have a specific pattern. The deflection conduit 30 is generally provided as a housing conduit to house a deflection means. Located within the deflection conduit 30 is a deflection member 40, such as a cable or wire, coaxially mounted within a spring sheath 64. The operation of the deflection means will be described in detail hereinafter. A delfection compensation means can also be provided in the core 28 such as is disclosed in co-pending U.S. patent application entitled "Endoscope Flexible Shaft having Deflection Compensation Means" by Wardle, Ser. No. 047,750 filed May 8, 1987 assigned to the assignee of the present application, which is incorporated by reference in its entirety herein.

The working conduit 32 is generally provided as the accessory passage or working channel for the instrument 2. The working channel 32 is connected at one end to the entry port 99 of the rotatable entry block 24 (see FIG. 3) at the first end 37 of the core with the opposite end of the working channel 32 being connected at the second end 38 of the core 28 to a working channel conduit 58 in the objective head 6 (see FIG. 4). The working conduit 32 of the core 28 thus is capable of allowing fluids and instruments introduced at the control head 4 to pass through the flexible shaft 8 and exit the objective head 6 to access the target area.

The two fiber-optic conduits 34 and 36 are generally provided to house the two light carriers or bundles of light transmitting fibers 44 and 46. As described above, the first light carrier 44 receives light from the external light carrier 18 at the light post/vent valve assembly 22. The first light carrier 44 travels through the control head 4 and through the conduit 34 of the core 28 to the objective head 6. The carrier 44 can thus provide light to the inspection site. A light image received from the illuminated site by the objective end optical system (not shown) is conveyed back to the eyepiece assembly 10 by the second internal light carrier 46 which travels from the objective head 6 through the conduit 36 and control head 4 to the assembly 10. In a preferred embodiment the carriers 44 and 46 are substantially free to move within the conduits 34 and 36 and due to the fact that the core is made of a flexible material, the light carriers can be contained in the conduits 34 and 36 without an additional protective sheath on the carriers. This can clearly help to reduce the cross-sectional size of the shaft 8. Although the core 28 has been described as having four internal conduits, other embodiments may include more or fewer conduits in addition to alternatively having the conduits located externally on the core 28.

As shown in the embodiment of FIG. 2, the core 28 has an exterior cover 66. The cover 66 in this embodiment, comprises a wire braid sheath 67 having an additional covering 69 of a polymer material. The wire braid 67 can be made of any suitable material, such as stainless steel, and in this embodiment, provides several functions for the shaft 8 along with the covering 69. First, the wire braid sheath provides a shaft torque stabilizing means to maintain a registry between the control head 4 and the objective head 6 in the event that the instrument must be twisted or torqued during insertion to a target area or alternatively to turn the objective head once the target area has been reached to allow for proper deflection of the distal end. Second, the additional covering 69 of polymer material provides a smooth surface for cooperative passage through channels such as channels in the human body. Third, it protects the flexible core 28 from externally caused damage that might occur through normal use and storage of the instrument. Fourth, the braid 67 can be connected to the core 28 to increase column or shaft strength over the length of the shaft 8.

In a preferred embodiment, the wire braid sheath 67 is selectively connected to the core 28 by means such as bonding by adhesive; however, any suitable connection means could be used. To provide for non-interference from the braid 67 during deflection of the distal end, the braid 67 is preferably not bonded to the core 28 adjacent the distal region of the shaft 8 such as section D in FIG. 3. Because the braid 67 is bonded selectively to the core 28, the polymer sheath 69 can also restrict the flexibility of the shaft, at least partially. However, this reduced flexability does not effect the distal region of the instrument 2, nor does it substantially interfere with the instrument's ability to navigate through tortuous channels. The bonding of the braid 67 to the core 28 stiffens the shaft 8 to give the shaft additional column strength to assist in insertion towards a target area and also prevents buckling. In addition, the outer covering 69 may either comprise a separate cover which is connected to or stretched over the wire sheath 67 or alternatively the outer cover 69 can be sprayed onto the braid 67. Alternatively, any type of cover or torque stabilizer means can be used with the core 28 or the core 28 may be used without a cover 66. However, the shaft 8, in the embodiment shown, has a shaft circumference of about ten (10) French or a diameter of about 3.33 mils.

Figure 3:
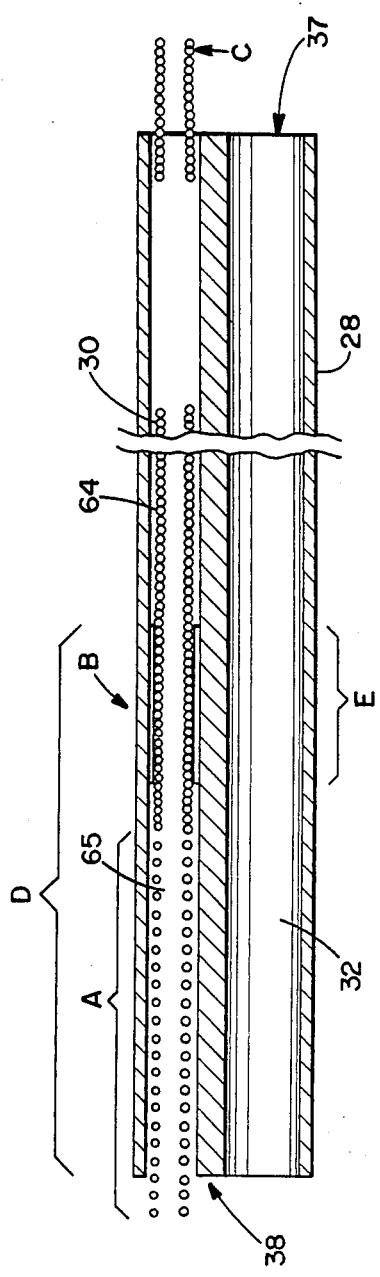
FIG. 3 is a cross-sectional side view of the core and the spring sheath used in the shaft of the instrument in FIG. 1 before total assembly of the shaft.

Referring now to FIG. 3, a cross-sectional side view of the core 28 having the spring sheath 64 mounted therein is shown before assembly of the entire instrument 2. The spring sheath 64 is located in conduit 30 and generally comprises a single member such as a wire which has been coiled or spiralled to form a single flexible tube-like structure. The spring sheath 64 may be made of any suitable material, but in a preferred embodiment the spring sheath 64 is made of stainless steel. The spring sheath 64, in this embodiment, has two types of sections; a forward distal end spring section A and a sheath section comprising the remaining portion of the spring sheath 64. The sheath section of the spring sheath 64 comprises side by side portions of the wire member being in close proximity to each other and, in this embodiment, the side by side portions of the wire member touch each other. The spring section A comprises the wire member of the spring sheath having a coil or spiral with an expanded spacing between side by side portions of the wire member. The expanded spacing between side by side portions creates spring-like properties in the forward section A such that spring section A acts like a spring. The spring section A may either be fabricated with the sheath 64 or alternately comprise the sheath 64 being deformed to form the spring section A. In an alternate preferred embodiment, the spring sheath 64 comprises two separate parts, a spring and a sheath. The spring and the sheath are mounted in the core 28 end to end with the sheath being bonded to the core and the spring being relatively free of any bonding to the core 28.

Generally, the spring sheath 64 can be mounted in the deflection conduit 30 by any type of method. However, the spring sheath 64 is preferably bonded to the core 28 selectively. In this embodiment, the spring sheath 64 is bonded to the core 28 at section B such that section A is substantially free to expand or contract without direct interference from the bond. As shown in the embodiment, before assembly, a portion of section A extends past the second end 38 of the core 28. In addition, a second portion C of the spring sheath 64 extends from the first end 37 of the core 28.

Figure 4:
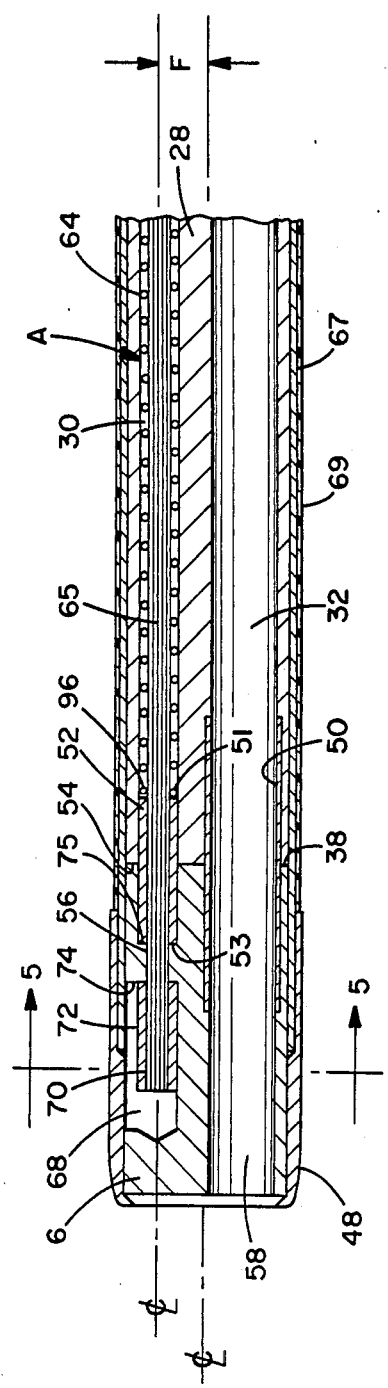
FIG. 4 is a cross-sectional side view of a distal region of the instrument in FIG. 1
Figure 5:
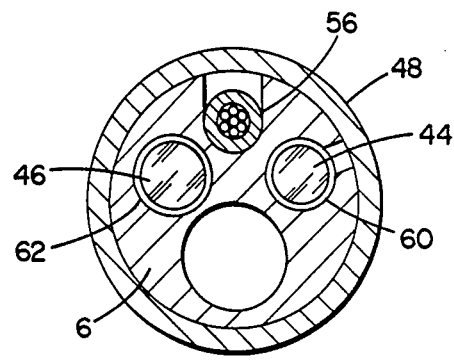
FIG. 5 is a cross-sectional view of the objective head assembly taken along line 5—5 in FIG. 4.

Referring now to FIG. 4, a cross-sectional side view of a portion of the distal region of the instrument 2 in FIG. 1 is shown. As shown in this embodiment, the distal region of the instrument 2 generally comprises the objective head 6, an objective head tip 48, a working channel sleeve 50, a deflection channel sleeve 52, a deflection collar 72 and a portion of the core 28 and braid 67 and polymer cover 69. A first end 54 of the objective head 6 generally abuts against the second end 38 of the core 28. The cross-sectional shape of the objective head, as shown in FIG. 5, is generally symmetrical to the cross-sectional shape of the core 28 such that the first end 54 of the objective head 6 and the second end 38 of the core 28 can be aligned. As shown in FIG. 5, the objective head 6 has four conduits or channels; a deflection channel 56, a working channel 58, and two fiber optic channels 60 and 62. The four objective head channels 56, 58, 60 and 62 are generally sized and orientated to match the cross-sectional shape of the channels in the core 28. The core 28 and the objective head 6 can thus be connected to each other with deflection conduit 30 aligned with deflection channel 56, working conduit 32 aligned with working channel 58, and fiber optics conduits 34 and 36 aligned with fiber optics channels 60 and 62, respectively.

Referring back to FIG. 4, the working channel sleeve 50 is provided to assist in aligning and maintaining alignment of the working channel 32 in the core 28 and working channel 58 in the objective head 6. The deflection channel sleeve 52 is provided to assist in aligning and maintaining alignment of deflection channel 30 in the core 28 and deflection channel 56 in the objective head 6. In addition, the deflection channel sleeve 52 also compresses the spring section A of the spring sheath 64 between the bonded section B (see FIG. 3) and a first end 51 of the sleeve 52. The resulting internal compressive force from the compressed spring section A is generally centered along the centerline of the deflection channel 30 which is offset from the centerline of the core 28 a distance F. The braid 67, although not attached to the portion of the core 28 designated by section D in FIG. 3, is connected to the remaining portion of the core 28 and the objective head 6. Thus, the braid 67 can prevent the core 28 and objective head 6 from being separated by the compressed spring portion A of the spring sheath 64. In an alternate embodiment, a separate spring may be provided in the distal region to replace or supplement the spring section A of spring sheath 64.

The spring sheath 64 is generally manufactured with a central passageway 65 within its tube-like structure which is intended to accommodate a control cable or wire 40. The cable 40 is connected at a first end, (not shown) to the deflection control 17 (see FIG. 1) in the control head 4. The cable 40 then travels from the control head 4 through the central passageway 65 of the spring sheath 64 in the conduit 30 to the objective head 6. The cable 40 passes through the deflection conduit sleeve 52, through the deflection conduit 56 in the objective head 6 into a slot 68 in the objective head 6 to form a cable second end 70. The deflection collar 72 is fixed on the cable second end 70 and abuts against a ledge 74 in the slot 68. The deflection sleeve 52 has the first end 51 that abuts against a second end 96 of the spring sheath 64 and a second end 53 that abuts against a face 75 on the objective head 6.

Figure 7:
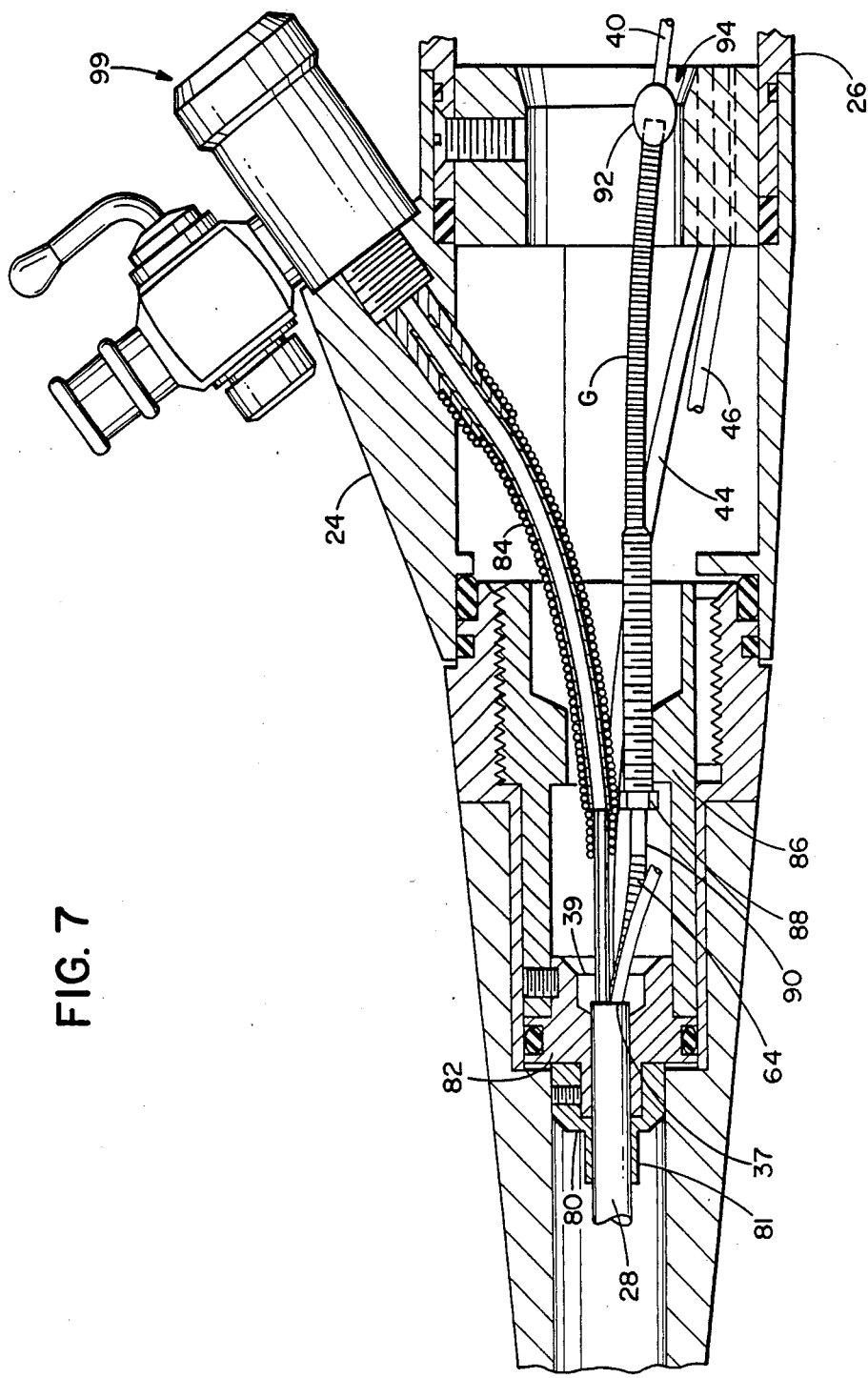
FIG. 7 is a partial cross-sectional side view of a forward portion of the control head of the instrument shown in FIG. 1.

Referring now to FIG. 7, a partial cross-sectional side view of a forward portion of the control head 4 of FIG. 1 is shown. In this embodiment, the first end 37 of the core 28 is mounted in a shaft end bushing 82. The fitting 80 has a collar 81 which the braid 67 (see FIG. 2) is connected to. The fitting 80 is connected to shaft end bushing 82 which is connected to a chassis 86 mounted to the housing 26. A working channel adapter tube 84 passes through the chassis 86 and connects the rotatable entry block 24 with the working channel 32 in the core 28. The two bundles of light transmitting fibers 44 and 46 travel through the chassis 86 and into their respective conduits 34 and 36 (not shown) in the core 28. An adhesive molding 39 is located in the bushing 82 adjacent the first end 37 of the core 28. The molding 39 allows for the proper attachment of the core 28 with the bundles 44 and 46, sheath 64 and adapter tube 84 as well as bonding the first end 37 of the core 28 with the bushing 82.

The spring sheath 64 and control cable 40 extend past the first end 37 of the core 28 and through a portion of the chassis 86. The cable 40 continues to the deflection control 17 (not shown); however, the spring sheath 64 ends at a first end 94. Located at the first end 94 of the spring sheath 64 is a solder joint 92 which fixedly connects the first end 94 of the spring sheath 64 to the cable 40. Located at a predetermined position on the spring sheath 64 is a stop sleeve 90 which is fixed to the exterior of the sheath 64, but not to the cable 40, and abuts a stop nut 88 connected to the chassis 86. The cable 40 and a portion G of the sheath 64 pass through the stop nut 88; however, the stop nut 88 and the stop sleeve 90 prevent any further advancement of the sheath 64 through the stop nut 88.

Referring now to FIGS. 4 and 7, the assembly of the deflection system of the instrument 2 will be generally described. The spring sheath 64 is mounted in the deflection conduit 30 of the core 28. The control cable 40 is passed through the central passageway 65 of the spring sheath 64. The objective head 6, deflection conduit sleeve 52 and working channel sleeve 50 are placed at the second end 38 of the core 28 with the two sleeves 50 and 52 aligning and maintaining alignment between the core 28 and the objective head 6. In addition, the deflection conduit sleeve 52 having the first end 51 adjacent the spring sheath second end 96 and the second end 53 adjacent the deflection sleeve face 75 in the objective head 6, compresses the spring section A of the spring sheath 64. The spring section A, desiring to expand, exerts a force between section B of the spring sheath 64 which is bonded to the core 28 and the first end 51 of the sleeve 52. The collar 72 is fixed to the distal end of the cable 40 and positioned in the slot 68 in the objective head 6. The braid 67 and tip 48 are soldered together and then connected to the objective head 6 with the braid 67 also being selectively connected to the core 28. The cover 66, although allowing the distal end to deflect, prevents the spring section A of the spring sheath 64 from separating the objective head 6 and core 28.

The spring sheath 64 and cable 40, which extend past the first end 37 of the core 28 are connected to the control head 4. The spring sheath 64 and cable 40 pass through the stop nut 88 on the chassis 86 and the stop sleeve 90 is fixed to a predetermined position on the spring sheath 64. The spring sheath 64 is pulled through the stop nut 88 until the the sleeve 90 abuts against the stop nut 88 and thereby prevents further movement of the spring sheath 64 through the nut 88. The stop nut 88 is adjustable to adjust the position of the sleeve 90. The nut 88 can be rotated clockwise or counter-clockwise to move a face on which the sleeve 90 makes contact. The first end 94 of the spring sheath 64 is then attached to the cable 40 and the first end of the cable 40 is connected to the deflection control 17 (not shown).

Before any tension is applied to the cable 40, the spring section A of the spring sheath 64 will cause a deflection at the distal end of the instrument 2. Generally, the following four factors come into effect in allowing the pre-tension deflection to occur. The objective head 6 and core 28 are connected to each other to prevent separation. The compressed spring section A located proximate the distal end has a tendency to expand. The compressed spring section A located proximate the distal end is offset from the longitudinal axis of the core 28. Finally, the core 28 is made of a resilient and flexible material which is capable of elastic deformation. The effect is that the distal end of the instrument 2 is deflected to a curved position as shown in FIG. 6a.

Figure 6C:
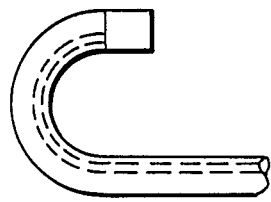
FIG. 6c is a perspective view of the distal region of the shaft shown in FIG. 6b having a deflection caused by a tension member.
Figure 6B:
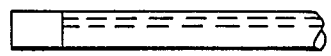
FIG. 6b is a perspective view of the distal region of the shaft shown in FIG. 6a having the distal region oriented in a substantially straight position.
Figure 6A:
FIG. 6a is a perspective view of the distal region of the instrument in FIG. 1 having a delfection caused by a distal end compression spring.

The deflection of the distal end as shown in FIG. 6a is caused by an unequal cross-sectional deformation of the core 28 as the spring section A expands. The material of the core 28 is deformed more adjacent the deflection conduit 30 than the material located on the opposite side of the longitudinal axis. The reasons for this unequal deformation is because the force being applied by the spring section A is offset from the longitudinal axis of the core 28 and the offset force decreases in magnitude in proportion to the distance from the force. This unequal deformation causes the distal end to deflect. The amount of deflection is generally dependent on such factors as the amount of potential energy the spring section A possess, the length of spring section A, the length of offset F, the diameter of the core and the degree of flexibility of the material of the core 28.

Obviously, the curved position of the distal end shown in FIG. 6a would not be very practical to use while inserting the instrument 2 through a relatively narrow channel. Therefore, in a preferred embodiment, the distal end is generally maintained in the position as shown in FIG. 6b wherein the distal end is substantially straight. In order to actively move the distal end from the position shown in FIG. 6a, the deflection control 17 (see FIG. 2) is activated by the physician to pull the cable 40.

As the operator activates the deflection control 17 to pull the cable 40 the length of the cable between the objective head 6 and the control head 4 is shortened and the cable 40 exerts an opposite, but not necessarily equal, force to the spring section A at the distal end of the instrument. The force that is created by the pulling of the cable 40 is transmitted from the cable 40 to the objective head 6 by the collar 72 which is fixed to the cable second end 70 and abuts against the ledge 74 in the slot 68 of the objective head 6. The force that is transmitted to the objective head 6 is also transmitted to the deflection conduit sleeve 52 because the second end 523 of the sleeve 52 abuts against the face 75. Thus, the force exerted by the cable 40 is transmitted to the core 28 by the abutting objective head 6 and to the spring section A by the abutting sleeve 52.

The amount of controlled deflection of the distal end is determined by the amount that the cable 40 has been pulled and this amount is variable by means of the deflection control 17 in the control head 4. If there is no tensile force on the cable 40 at the distal region, the distal region will deflect as shown in FIG. 6a. If the tensile force on the cable 40 at the distal end is substantially equal to the force of the spring section A, then the distal region will appear substantially straight or undeflected as shown in FIG. 6b. If the tensile force on the cable 40 of the distal end is greater than the force of the spring section A, then the flexible material of the core 28 will deform and the distal end will deflect as shown in FIG. 6c.

To further explain the deflection shown in FIG. 6c, if the force exerted by the cable 40 is greater than the force of the spring section A, the objective head 6 and deflection sleeve 52 will tend to compress the material in the core 28 and the spring section A, respectively. Since the material of the core 28 is flexible and resilient, the force exerted by the cable 40 through the objective head 6 will elastically deform the core 28. Since the cable 40 is offset by the distance F from the longitudinal axis of the core 28, an unequal cross-sectional deformation of the core will occur. The offset force will generally compress the core 28 more proximate the deflection conduit 30 and less on the opposite side of the longitudinal axis of the core 28 and may in fact cause tension in the core opposite the deflection conduit 30. Preferably, the distal end of the instrument can deflect about 180 degrees in this manner and the amount of deflection is dependent on the amount of pull or force on the cable 40.

Referring also to FIG. 7, as the cable 40 is pulled by the deflection control 17 (not shown) the first end 94 of the spring sheath 64 is also pulled with the cable 40 because of the solder joint 92. However, the spring sheath 64 located in front of the stop sleeve 90 does not move because of the stopping contact between the stop sleeve 90 fixed to the sheath 64 and the stop nut 88. The result is that the spring sheath 64 located between the stop sleeve 90 and the solder joint 92 expands elastically due to the spring coils of the sheath 64. This exerts a force on the cable 40 at the solder joint 92, which is ordinarily overcome by the deflection control 17 (not shown).

After deflection of the distal end, the operator can decrease the amount of deflection, straighten the distal end or deflect the distal end in the opposite direction. To change the amount of deflection the operator can, at least partially, inactivate the deflection control 17 (not shown) which will then release a portion of the cable 40 to allow for a lengthening of the cable 40 located between the objective head 6 and the control head 4. The additional available length of the cable 40 allows the spring section A at the distal end, which had been compressed, to expand and allows the deformed material of the core 28 to, at least partially, recover from its deflected position. The greater the amount of the lengthening of the cable 40 between the objective head 6 and the control head 4, the greater the amount of recovery from the deflected position until a substantially straight position is obtained.

If an additional amount of cable 40 is released from the deflection control 17 after the substantially straight position is obtained, then the spring section A of the spring sheath 64 will cause an opposite deflection as initially described above. Thus, a two way deflection is available in the distal end. However, in a preferred embodiment, the cable 40 has a maximum length between the objective head 6 and the control head 4 substantially equal to the length of the core 28 to establish a substantially straight home position as shown in FIG. 6b and having only a one way deflectable distal end.

The portion of the spring sheath 64 located between the stop sleeve 90 and the solder joint 92, which had also been expanded during the pulling of the cable 40 by the deflection control 17 (see FIG. 2), assists in pulling the cable 40 from the deflection control 17 and pushing the cable 40 through the spring sheath 64 to assist the spring section A and also help overcome any resistance or friction between the cable 40 and the spring sheath 64.

Various alternate embodiments can be devised by the use of a flexible core and deflection means. One embodiment could have an instrument with only a distal region spring. A second embodiment could have an instrument with only a proximal region spring. A third embodiment could have an instrument with no springs wherein a compressively stable wire is used to push against the objective head at a distance offset from the longitudinal axis rather than pulling on the objective head. In a fourth embodiment, a compressively stable wire could be used with either a proximal region spring or a distal region spring or both. In yet another embodiment more than one cable and spring sheath could be used for deflection and deflection recovery in three and four way deflectable instruments. The springs could also be either tension or compression springs or the springs could be replaced by equivalent deflection recovery means.

Figure 8:
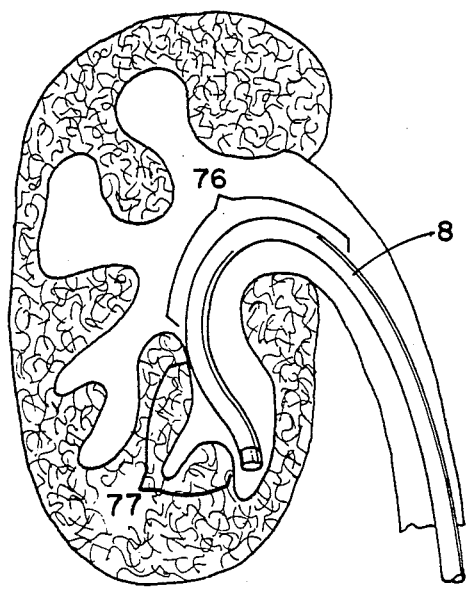
FIG. 8 is a diagrammical view of a human kidney having the distal end of the instrument in FIG. 1 therein.

In addition to active deflection and recovery of the distal region, the instrument 2 can also possess passive deflection. Referring to FIGS. 3 and 8, FIG. 8 is a diagrammatic view of the distal region of the instrument 2 of FIG. 1 having a passive deflection section 76 in use in a human kidney. The passive deflection section 76, although not having active deflection as seen in section 77 which is controlled by the deflection control 17, can be used to direct the distal region by rebounding the shaft 8 off of the area being examined. The passive deflection section 76, in this embodiment, is generally located behind the spring section A. Passive deflection section 76 is deflectable in order to assist the active deflection section in reaching hard to reach places. In this embodiment, the wire braid sheath is not bonded to the core 28 at section D to thus allow the active and passive deflection sections to deflect properly. Thus, the flexible shaft 8, in this embodiment, is capable of both active controlled deflection and passive deflection in reaching a target area. In an alternate embodiment, the wire braid 67 is not bonded to the core 28 along section D, in addition, the spring sheath 64 does not have a bond B at section E which will create an elliptical deflection at the distal end.

It should be under stood that the foregoing description is only illustrative of the invention. Various alternatives and modifications can be devised by those skilled in the art without departing from the spirit of the invention. Accordingly, the present invention is intended to embrace all such alternatives, modifications and variances which fall within the scope of the appended claims.

What is claimed is:

1. An instrument of a generally tubular flexible shape for accessing a target area, the instrument having a proximal region thereof, a distal region thereof, and a shaft therebetween, said shaft comprising:
   structural core means of a substantially flexible and resilient material having a first longitudinal axis, said core means forming a flexible frame which can cooperate in conveying the distal region of the instrument towards the target area while also defining a conduit means therewith; and
   deflection means disposed on said flexible core means, said deflection means being connected to said distal region at an offset from said first longitudinal axis whereby upon activation of said deflection means said distal region is deflected.

2. An instrument as in claim 1 further comprising a deflection recovery means.

3. An instrument as in claim 2 wherein said recovery means comprises a distal region spring means.

4. An instrument as in claim 2 wherein said recovery means comprises a proximal region spring means.

5. An instrument as in claim 2 wherein said deflection recovery means comprises a spring sheath having a proximal end spring section and a sheath section.

6. An instrument as in claim 1 further comprising a shaft torque stabilizer means.

7. An instrument as in claim 5 wherein said torque stabilizer means is selectively connected to said core means.

8. An instrument as in claim 7 wherein said torque stabilizer means is substantially unfastened to said core means adjacent said distal region.

9. An instrument as in claim 1 wherein said core means is a polymer material.

10. An instrument as in claim 1 wherein said deflection means comprises a tension means.

11. An instrument as in claim 1 wherein said deflection means comprises a compression means including a compressively stable connection member.

12. An instrument as in claim 1 wherein said shaft is about 10 French in circumference.

13. An instrument as in claim 1 wherein said shaft further comprising passive deflection means.

14. An instrument of a generally tubular flexible shape for accessing a target area, the instrument having a proximal region thereof, a distal region thereof, a shaft therebetween having a longitudinal axis and deflection means for deflecting said distal region, said deflection means comprising:
   a deflection member disposed on a channel on said shaft, said deflection member having a distal portion connected to said distal region at a position offset from said longitudinal axis and a proximal portion operably connected to said proximal region;
   deflection member control means for deflecting said distal region from a home position to a deflected position; and
   deflection recovery means for at least partially automatically returning said distal region from said deflected position to said home position as said control means is inactivated.

15. An instrument as in claim 14 wherein said deflection recovery means comprises a distal region spring means.

16. An instrument as in claim 14 wherein said deflection recovery means comprises a proximal region spring means.

17. An instrument as in claim 15 wherein said spring means forms a sheath about said deflection member.

18. An instrument as in claim 14 wherein said home position has said distal region in a substantially straight position.

19. An instrument as in claim 14 wherein said home position has said distal region in a substantially curved position.

20. A method of manufacturing an instrument of a generally tubular flexible shape of accessing a target area, the instrument having a proximal region thereof, a distal region thereof, a shaft therebetween, and a deflection means, the method comprising the steps of:

mounting a deflection member on a channel means of a structural core of flexible material, said core having a first longitudinal axis, said deflection member being offset from said first longitudinal axis proximate said distal region; and mounting a deflection recovery means on said core, said deflection recovery means comprising a spring means connected to said distal region at an offset, proximate said distal region, from said first longitudinal axis whereby said distal region is deflectable and said deflection recovery means cooperates to return said distal region to an undeflected position.

* * * * *